(12) United States Patent
Garson et al.

(10) Patent No.: US 11,992,661 B2
(45) Date of Patent: *May 28, 2024

(54) INJECTION DEVICE FILL VOLUME MANAGEMENT

(71) Applicant: Owen Mumford Limited, Woodstock (GB)

(72) Inventors: Daniel Garson, Woodstock (GB); Andreas Artelsmair, Woodstock (GB); Matthew John Dobson, Woodstock (GB); Andrew Hung, Woodstock (GB); Abiodun Falodi, Woodstock (GB); Robert Dutton, Woodstock (GB); Marco Caglio, Woodstock (GB)

(73) Assignee: Owen Mumford Limited, Oxfordshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/840,740

(22) Filed: Jun. 15, 2022

(65) Prior Publication Data

US 2022/0313920 A1 Oct. 6, 2022

Related U.S. Application Data

(63) Continuation of application No. 16/585,322, filed on Sep. 27, 2019, now Pat. No. 11,383,040.

(30) Foreign Application Priority Data

Sep. 28, 2018 (GB) ...................................... 1815826

(51) Int. Cl.
*A61M 5/315* (2006.01)
*A61M 5/20* (2006.01)
*A61M 5/32* (2006.01)

(52) U.S. Cl.
CPC ...... *A61M 5/31515* (2013.01); *A61M 5/2033* (2013.01); *A61M 5/31585* (2013.01);
(Continued)

(58) Field of Classification Search
CPC ............ A61M 5/31515; A61M 5/2033; A61M 5/31585; A61M 5/3202; A61M 2005/2026; A61M 2005/2073; A61M 2207/00
(Continued)

(56) References Cited

U.S. PATENT DOCUMENTS 11,383,040 B2 * 7/2022 Garson ............... A61M 5/2033
2003/0004467 A1 1/2003 Musick et al.
(Continued)

FOREIGN PATENT DOCUMENTS

CN 104703643 A 6/2015
CN 105102019 A 11/2015
(Continued)

OTHER PUBLICATIONS

GB Search Report, dated Mar. 22, 2019, from corresponding GB application No. 1815826.1.
(Continued)

*Primary Examiner* — Theodore J Stigell
*Assistant Examiner* — Nidah Hussain
(74) *Attorney, Agent, or Firm* — Quarles & Brady LLP

(57) ABSTRACT

An apparatus for a firing mechanism 102 for use in an injection device 100 and comprising: a rear cap 104 having an elongate member 110 extending axially forwards when installed within the injection device; a plunger 106 releasably connected, directly or indirectly, to the elongate member and, upon release of the connection to the elongate member, axially displaceable in a forward direction; and a plunger driver 112 to drive the plunger axially forwards
(Continued)

upon release of the connection to the elongate member, wherein the plunger and the rear cap define an axial length of the assembly, which in turn determines a start position of a forward end of the plunger before release of the connection to the elongate member, and wherein, during construction of the assembly, the plunger is releasably connectable, directly or indirectly, to the elongate member at one of a plurality of positions for controlling the axial length of the assembly.

16 Claims, 9 Drawing Sheets

(52) U.S. Cl.
CPC ... *A61M 5/3202* (2013.01); *A61M 2005/2026* (2013.01); *A61M 2005/2073* (2013.01); *A61M 2207/00* (2013.01)

(58) Field of Classification Search
USPC .......................................... 604/110
See application file for complete search history.

(56) References Cited

U.S. PATENT DOCUMENTS

| | | |
|---|---|---|
| 2008/0262436 A1 | 10/2008 | Olson |
| 2010/0185178 A1 | 7/2010 | Sharp |
| 2013/0046238 A1 | 2/2013 | Edhouse et al. |
| 2013/0296795 A1* | 11/2013 | Ekman .................. A61M 5/326 74/99 A |
| 2013/0317448 A1* | 11/2013 | Hourmand .......... A61M 5/2033 604/197 |
| 2014/0257193 A1* | 9/2014 | Bostrom ............. A61M 5/2033 604/197 |
| 2014/0330216 A1 | 11/2014 | Weaver et al. |
| 2017/0266385 A1 | 9/2017 | Farris |
| 2020/0101231 A1* | 4/2020 | Garson ............... A61M 5/2033 |

FOREIGN PATENT DOCUMENTS

| | | |
|---|---|---|
| CN | 106029127 A | 10/2016 |
| CN | 206325076 U | 7/2017 |
| EP | 2 586 478 A2 | 5/2013 |
| WO | 2007066152 A3 | 8/2007 |
| WO | 2015074975 A1 | 5/2015 |
| WO | 2016118688 A1 | 7/2016 |
| WO | 2018007623 A1 | 1/2018 |

OTHER PUBLICATIONS

Extended European Search Report issued in European Patent Application No. 19198992.0 dated Nov. 20, 2019.

First Office Action from corresponding Chinese Patent Application No. 201910931503.3 dated May 24, 2021 (13 pages) (partial English translation included).

China National Intellectual Property Administration. First Office Action from corresponding China Patent Application No. 202210694399.2, issued Apr. 26, 2023 [14 pgs] [English translation included].

* cited by examiner

INJECTION DEVICE FILL VOLUME MANAGEMENT

CROSS-REFERENCE TO RELATED APPLICATIONS

The present application is a continuation application of U.S. Ser. No. 16/585,322 filed Sep. 27, 2019, which relates to and claims priority benefits from British Patent Application Serial No. GB 1815826.1, filed on Sep. 28, 2018, the contents of which are incorporated herein by reference in their entirety.

TECHNICAL FIELD

The invention relates to injection devices for delivering a fluid substance to a user or patient via a syringe. In specific arrangements, the invention relates to, but need not be limited to, auto-injectors for delivering the fluid under a force applied by a drive system.

BACKGROUND

Injection devices are used for the convenient administration of medicaments to patients. For example, injection devices, which may be auto-injectors, may be used for providing a single metered dose of a medicament. Such devices may be either single use "disposable" devices in which the device is typically provided with a syringe already installed, and which is not user-replaceable, or "reusable" devices which allow the user to replace the syringe when the medicament has been used.

It is noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may be formed integrally with the (or part of the) injection device.

Injection devices may be provided in the form of an auto-injector device, in which delivery of the medicament is automated and the device may also be arranged to automate the insertion of a needle into the skin prior to the delivery of the medicament. However, it is noted that the term auto-injector may encompass injection devices that automatically insert the needle and devices which require the user to manually insert the needle.

Injection devices generally comprise a firing mechanism that is arranged to deliver a fluid from the syringe automatically under the force of a drive system, such as a drive spring. Optionally, injection devices may also comprise an insertion mechanism to displace the syringe within a housing of the injection device to cause needle penetration. The delivery arrangement generally acts via a plunger which includes a plunger and may also include or engage a piston (also referred to as a "bung") which is slidably provided within the syringe.

Injection devices may be designed and manufactured to accommodate different syringes. This provides a device that may be adapted to carry and operate syringes with different features and/or characteristics, such as different fill volumes. It is desirable to improve the safety and operability of such devices.

SUMMARY

Different syringes may be filled with different volumes of fluid, such as medicament. A difference in fill volume of a syringe results in a different axial position of the bung prior to use of the syringe as it is the bung that sets the useable volume within the barrel of the syringe. The inventors have realised that where a gap exists between an end of the plunger and the bung, e.g. because the fill volume is relatively low, the plunger moves in free space for a distance before engaging the bung. This movement in free space can cause the plunger to accelerate to velocities that are too high, such that when the plunger contacts the bung, damage may be caused to the syringe and discomfort may be caused to the recipient of an injection.

Methods and apparatus disclosed herein may be arranged to mitigate or solve one or more problems associated with the art, including those mentioned above and/or elsewhere herein.

According to the invention in an aspect, there is provided an assembly for a firing mechanism for use in an injection device and comprising: a rear cap having an elongate member extending axially forwards when installed within the injection device; a plunger releasably connected, directly or indirectly, to the elongate member and, upon release of the connection to the elongate member, axially displaceable in a forward direction; and a plunger driver to drive the plunger axially forwards upon release of the connection to the elongate member, wherein the plunger and the rear cap define an axial length of the assembly, which in turn determines a start position of a forward end of the plunger before release of the connection to the elongate member, and wherein, during construction of the assembly, the plunger is releasably connectable, directly or indirectly, to the elongate member at one of a plurality of positions for controlling the axial length of the assembly.

By controlling the length of the axial length of the assembly, the acceleration of the plunger under the force of the plunger driver before contacting the bung may be controlled. Further, it should be noted that the plurality of positions of the releasable connection may be discrete positions or may be a continuously varying.

Optionally, one or both of the plunger and the elongate member comprises a plurality of connection features for connection between the plunger and the elongate member during construction of the assembly.

Optionally, the plurality of connection features comprises a plurality of recesses or apertures on the elongate member, and wherein the plunger comprises a lug configured to be received in one of the plurality of recesses or apertures.

Optionally, the elongate member comprises an axially extending channel and wherein the recesses extend from a sidewall of the channel.

Optionally, the lug of the plunger is configured to travel within the channel and to enter one of the recesses on relative rotation between the plunger and the elongate member.

Optionally, the assembly further comprises a clutch that is rotationally coupled to the plunger, such that rotation of the clutch causes rotation of the plunger, and the clutch is configured to rotate upon activation of the injection device to rotate the plunger and move the lug from one of the plurality of recesses into the channel, to release the connection between the plunger and the elongate member.

Optionally, the plurality of connection features comprises a plurality of recesses or apertures on one of the plunger and the elongate member, and wherein the other of the plunger and the elongate member comprises a prong radially biased and having a resting position configured to engage a projection of the prong with one of the plurality of recesses or apertures.

Optionally, the plunger comprises the plurality of connection features and the rear cap comprises the prong.

Optionally, the rear cap comprises the plurality of connection features and the plunger comprises the prong.

Optionally, the assembly further comprises a clutch positioned around the plunger or the rear cap such that an inner wall of the clutch is presented to the prong, wherein the clutch has a first inner diameter and a second inner diameter greater than the first inner diameter, and wherein the clutch is moveable between a first position in which the first diameter is presented to the prong and prevents radially outward displacement thereof, and a second position in which the second diameter is presented to the prong and provides a space between the prong and the inner wall of the clutch, allowing radially outward displacement of the prong.

Optionally, the rear cap comprises a keyed aperture, and the plunger comprises a plurality of keyed sections having a cross section corresponding to the keyed aperture and at least one lockout section positioned between the keyed sections and configured to permit rotation of the plunger within the keyed aperture.

Optionally, the assembly further comprises a plunger carrier releasably connected to the elongate member, the plunger being connected to the plunger carrier, such that the plunger is indirectly releasably connected to the elongate member, wherein, during construction of the assembly, the plunger is connectable to the plunger carrier at one of a plurality of positions for controlling the axial length of the assembly.

Optionally, one or both of the plunger and the plunger carrier comprises a plurality of connection features for connection between the plunger and the plunger carrier during construction of the assembly.

Optionally, the plunger is connectable to the plunger carrier by a thread on one of the plunger and the plunger carrier and a thread engagement feature on the other of the plunger and the plunger carrier comprises.

Optionally, the plunger carrier comprises a plurality of abutment surfaces at a plurality of axial positions on the plunger carrier, and the plunger comprises a corresponding configured to abut one of the abutment surfaces.

Optionally, the plunger is telescopically received within the elongate member.

According to the invention in an aspect, there is provided an injection device comprising the assembly according to any preceding claim.

According to the invention in an aspect, there is provided a method of constructing an assembly for a firing mechanism for an injection device, the method comprising: releasably connecting, directly or indirectly, a plunger to an elongate member of a rear cap, the plunger being axially displaceable in a forward direction upon release of the connection to the elongate member, wherein the plunger and the rear cap define an axial length of the assembly, which in turn determines a start position of a forward end of the plunger before release of the connection to the elongate member, and wherein the releasable connection is made at any of a plurality of positions to control the axial length of the assembly.

BRIEF DESCRIPTION OF THE DRAWINGS

Exemplary embodiments will be described herein with reference to the accompanying drawings, in which.

DETAILED DESCRIPTION

Generally, disclosed herein are methods and apparatus for controlling a gap between a bung of a syringe and a forward end of a plunger prior to activation of an injection device. For the remainder of this document, the term "auto-injector" will be used in place of "injection device" in order to aid description of some specific embodiments. However, this should not be seen as limiting.

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use.

Many features of the exemplary arrangements disclosed herein are described as being "coupled" to other features. This term encompasses any coupling that results in the coupled features moving together in any direction, whether that be on a 1:1 basis or on some geared basis. The term "coupled" also encompasses any one of a connection between features, an abutment of one feature against another and an engagement of one feature with another, and such coupling may be direct or may be indirect, i.e. with a third feature therebetween.

Figure 1:
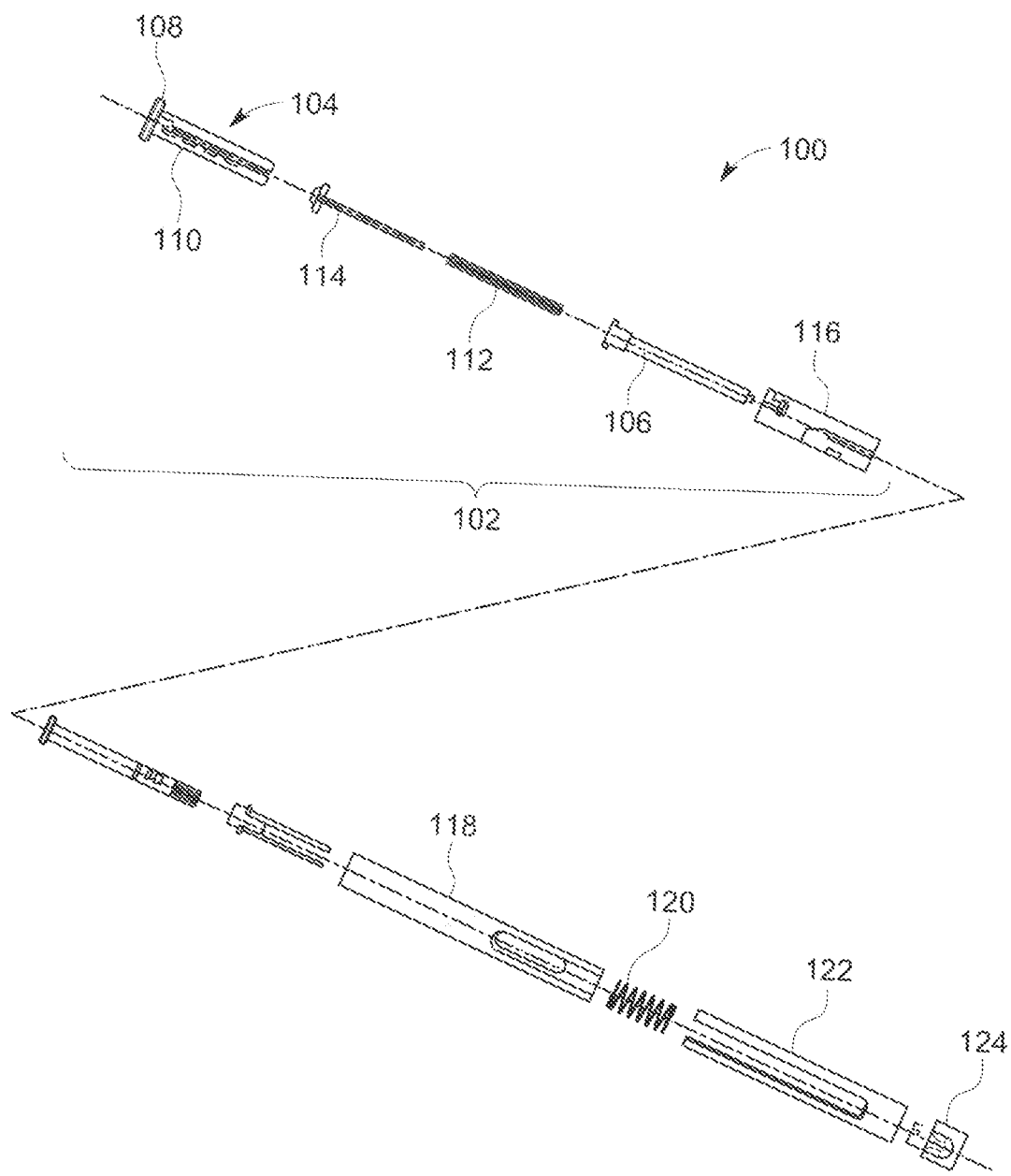
FIG. 1 is an exploded view of an auto-injector.

FIG. 1 shows an exploded view of an auto-injector 100. The auto-injector 100 comprises a firing assembly 102. The firing assembly comprises a rear cap 104 and a plunger 106. The rear cap 104 comprises a head 108 and an elongate member 110. The rear cap 104 and the plunger 106 are connected to each other such that before firing, relative axial movement between them is resisted or prevented. The connection between the rear cap 104 and the plunger 106 is releasable such that after activation of the auto-injector 100, relative axial movement between them is permitted. The nature of the releasable connection is discussed in more detail below. As used herein, the term "axial" encompasses a direction parallel to or aligned with a longitudinal axis of the injection device.

The firing assembly 102 also comprises a biasing member 112 for driving the plunger 106 axially forwards and into a barrel of a syringe (shown in FIG. 2) retained within the auto-injector 100. In one example the biasing member 112 is a drive spring (e.g. a compression spring) and will be referred to as such throughout, although this should not be construed as limiting and the skilled person will appreciate that other means may be used to drive the plunger forwards.

Figure 2:
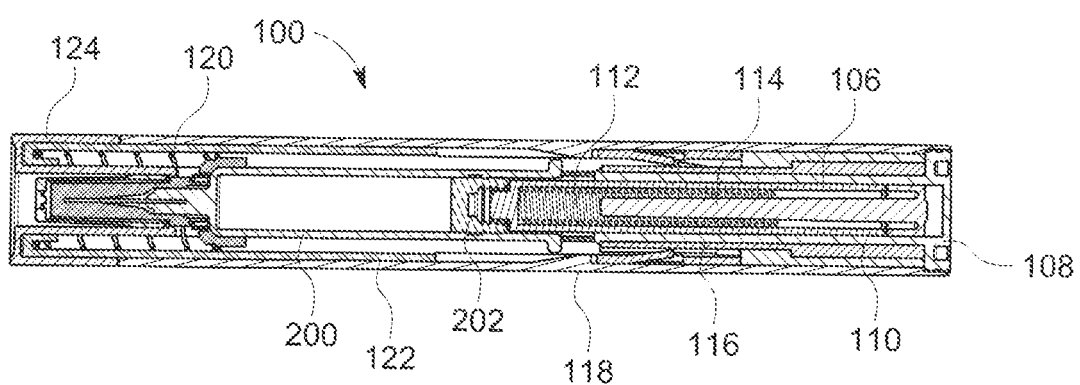
FIG. 2 is a section through an auto-injector with a syringe fitted therein.

In the example of FIG. 1, the plunger 106 is telescopically received within the elongate member 110 of the rear cap 104. The drive spring 112 is positioned between the rear cap 104 and the plunger 106 such that they are biased in opposite axial directions relative to each other. This is best shown in FIG. 2, which is a section through an auto-injector 100 in an assembled state before activation and with a syringe 200 retained therein. The plunger 106 is received within the elongate member 110. The plunger (106) is a hollow tube with an open end at the rear and the drive spring 112 is received within the plunger 106. A first end of the drive spring 112 abuts a forward end of the plunger 106 and a second end of the drive spring 112 is fixed with respect to the rear cap at least during delivery of a medicament from the syringe. In some exemplary arrangements, the second end of the drive spring 112 may be coupled to (i.e. directly or indirectly abuts or is connected to) a reaction surface on the rear cap 104 or a further member directly or indirectly axially coupled to the rear cap 104. In the example of FIG. 2, the drive spring 112 is coupled to an end of dose indicator 114, which in turn is coupled to the rear cap 104. Expansion of the drive spring 112 drives the plunger 106 forwards into the barrel of the syringe 200 because, in the example of FIGS. 1 and 2, the position of the rear cap 104 is fixed.

In FIG. 2, a forward end of the plunger (106) is shown abutting a bung 202. This will not always be the case, as discussed above.

The auto-injector 100 also comprises a clutch 116, which is positioned around the elongate member 110. Before activation of the auto-injector 100, the clutch 116 is rotationally coupled to the plunger 106. Rotation of the clutch 116 therefore causes rotation of the plunger 106. As explained below, on activation of the auto-injector 100, the clutch 116 rotates, thereby rotating the plunger 106 relative to the rear cap 104 to release the connection therebetween. Operation of the clutch 116 is explained in more detail below.

The auto-injector 100 also comprises a main body 118, which houses the firing mechanism 102, the syringe 200 and other features necessary for operation of the auto-injector 100. The main body 118 may comprise a plurality of separate parts. The main body 118 comprises a syringe locator, which in exemplary arrangements comprises one or more features for receiving and optionally retaining a syringe in position within the main body 118.

The auto-injector also comprises a lockout spring 120 and lockout shroud 122, wherein the lockout spring 120 is configured on release thereof to displace the lockout shroud 122 axially forwards to cover a needle of the syringe. A cap 124 also forms part of the auto-injector and covers a needle or forward end of the auto-injector prior to use.

Figures 3A, 3B:
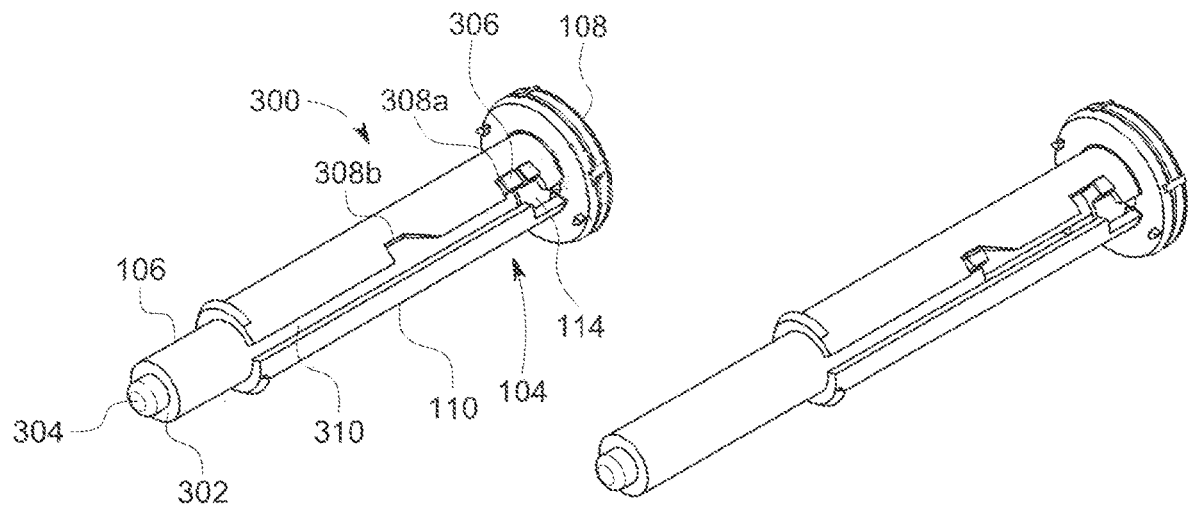
FIGS. 3a and 3b show perspective views of exemplary firing mechanism assemblies.

FIGS. 3a and 3b show perspective views of an assembly 300 for a firing mechanism. The assembly 300 comprises the rear cap 104 and the plunger 106. The plunger 106 is telescopically received within the elongate member 110. The assembly 300 also comprises a plunger driver to drive the plunger 106 axially forwards, which in the exemplary arrangements disclosed herein comprises a compression spring although the skilled person will understand that other arrangement are possible. The exemplary assembly 300 also comprises an end of dose indicator 114, but this feature is not essential and its operation is beyond the scope of this description.

The exemplary plunger 106 comprises a cylindrical tube that is open at a rear end and closed at a forward end. The forward end of the plunger 106 comprises a shoulder 302 and a projection 304 configured to engage a bung 202 in a syringe barrel. The plunger 106 also comprises a lug 306 configured to engage with any of a plurality of recesses 308a, 308b in the elongate member 110. In the exemplary arrangements of FIGS. 3a and 3b the lug 306 extends radially from on outer surface of the plunger 106.

The elongate member 110 comprises an axial channel 310. The plurality of recesses 308a, 308b are formed in a sidewall of the channel 310. That is, the plurality of recesses 308a, 308b extend circumferentially (or transverse to the axial channel) around the outer wall of the elongate member 110. It is noted that while only two recesses 308a, 308b are shown in FIGS. 3a and 3b, more recesses (e.g. three—as shown in FIG. 4—or four) may be provided in the elongate member 110. The recess 308b comprises an angled rear surface and a front surface that is perpendicular to an axial direction (or longitudinal axis) of the auto-injector 100. The recesses 308a, 308b are configured to receive the lug 306 of the plunger 106. FIG. 3a shows the lug 306 received in a rearward recess 308a and FIG. 3b shows the lug 306 received in a forward recess 308b.

The channel 310 and the recesses 308a, 308b are configured such that rotation of the plunger 106 relative to the elongate member 110 in a first direction moves the lug 306 into the recesses 308a, 308b and rotation in a second, opposite direction moves the lug 306 out of the recesses 308a, 308b.

The plunger 106 and the rear cap 104, in particular the elongate member 110, define an axial length of the assembly 300. The axial length of the assembly 300 determines a start position of the forward end of the plunger 106 before release of the connection of the plunger 106 the elongate member 110. This can be seen in FIGS. 3a and 3b, which show the plunger 106 releasably connected to the elongate member 110 at different points, thereby controlling the overall axial length of the assembly 300.

During assembly, the plunger 106 is connected to the elongate member 110 at any of a plurality of positions on the elongate member 110 and/or the plunger 106 to alter a combined axial length of the plunger 106 and the elongate member 110. The connection may be made directly or indirectly through a plunger carrier, as explained below. In the example of FIGS. 3a and 3b, a direct connection is made. The plunger 106 may be received within the elongate member 110 such that the lug 306 is in the channel 310. The plunger 106 may then be displaced relative to the elongate member 110 until the lug 306 is aligned with one of the recesses 308a, 308b. The plunger 106 may then be rotated such that the lug is received within the one of the recesses 308a, 308b with which it was aligned. The force provided by the drive spring 112 retains the lug 306 within the recess 308a, 308b against the forward surface thereof. The combined axial length of the assembly (i.e. of the rear cap 104 and the plunger 106) is increased in FIG. 3b when compared to FIG. 3a, in which the lug 306 is received within the rearward recess 308a.

Figures 4A, 4B:
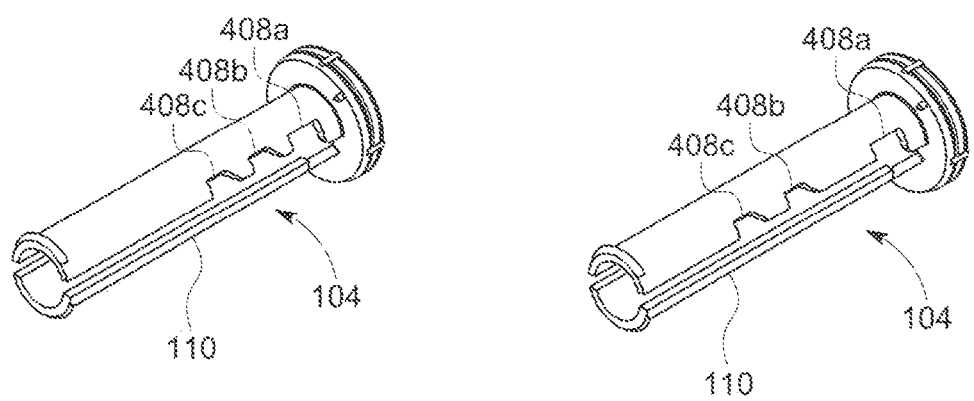
FIGS. 4a and 4b show perspective views of exemplary rear caps.

FIGS. 4a and 4b show alternative rear caps 104 having three recesses 408a, 408b, 408c. It will be appreciated that other numbers of recesses may be used. In addition, the recesses 408a, 408b, 408c may be positioned at any point on the elongate member 110. In the exemplary arrangement of FIG. 4b, the recesses 408b and 408c have been displaced forwards with respect to those in FIG. 4a.

Figure 5:
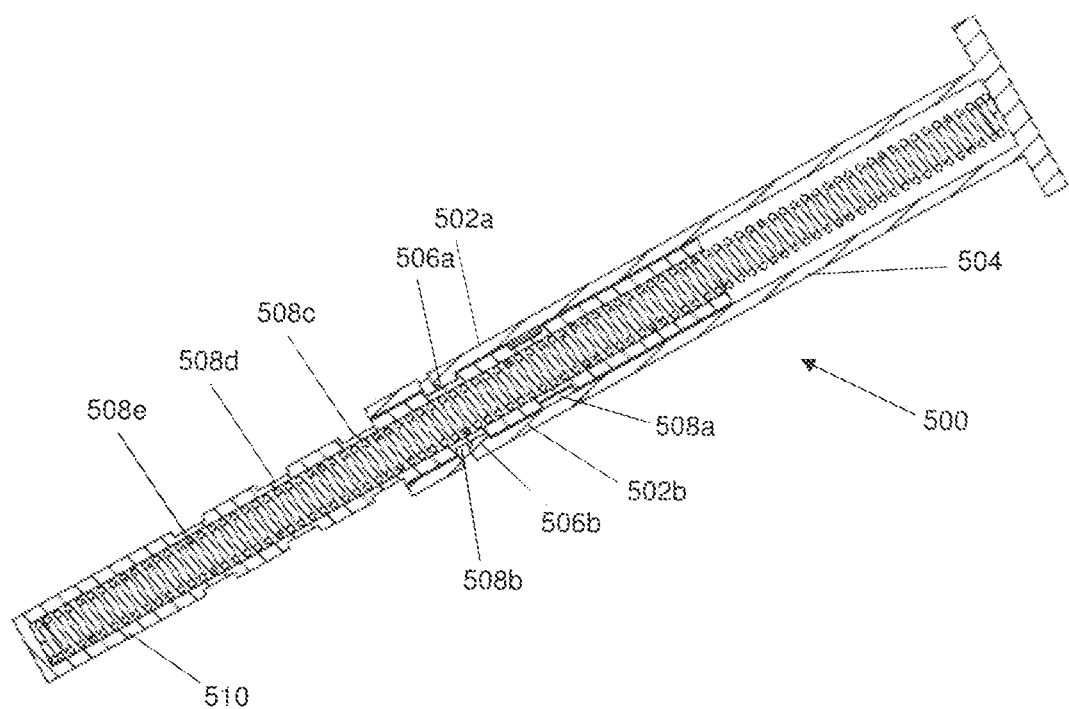
FIG. 5 shows an exemplary firing mechanism assemblies.

Other configurations of plunger and rear cap are possible. For example, FIG. 5 shows a rear cap 500 having at least one elastic prong 502 positioned on the elongate body 504. In exemplary arrangements, the rear cap 500 comprises two prongs 502a, 502b, which are elastic. The elastic prongs 502a, 502b comprise projections 506a, 506b extending radially inwards. The projections 506a, 506b are configured to engage corresponding features 508a-508e of the plunger 510. In the example shown in FIG. 5, the features 508a-508e of the plunger 510 comprise recesses or apertures into which the projections 506a, 506b may be received. The elastic prongs 502a, 502b have a resting position in which the projections are received in the recesses of the plunger 510 and are biased radially inwards such that a force is required to displace them radially outwards. The projections 506a, 506b are thereby retained in the recesses of the plunger 510.

In FIG. 5, the recesses are formed by varying the diameter of the plunger 510. In other arrangements, an alternative plunger 512 may comprise recesses formed by discrete apertures. The skilled person will be able to think of a number of different options for providing the features on the plunger corresponding to and for receiving the projections 506a, 506b.

Figure 6:
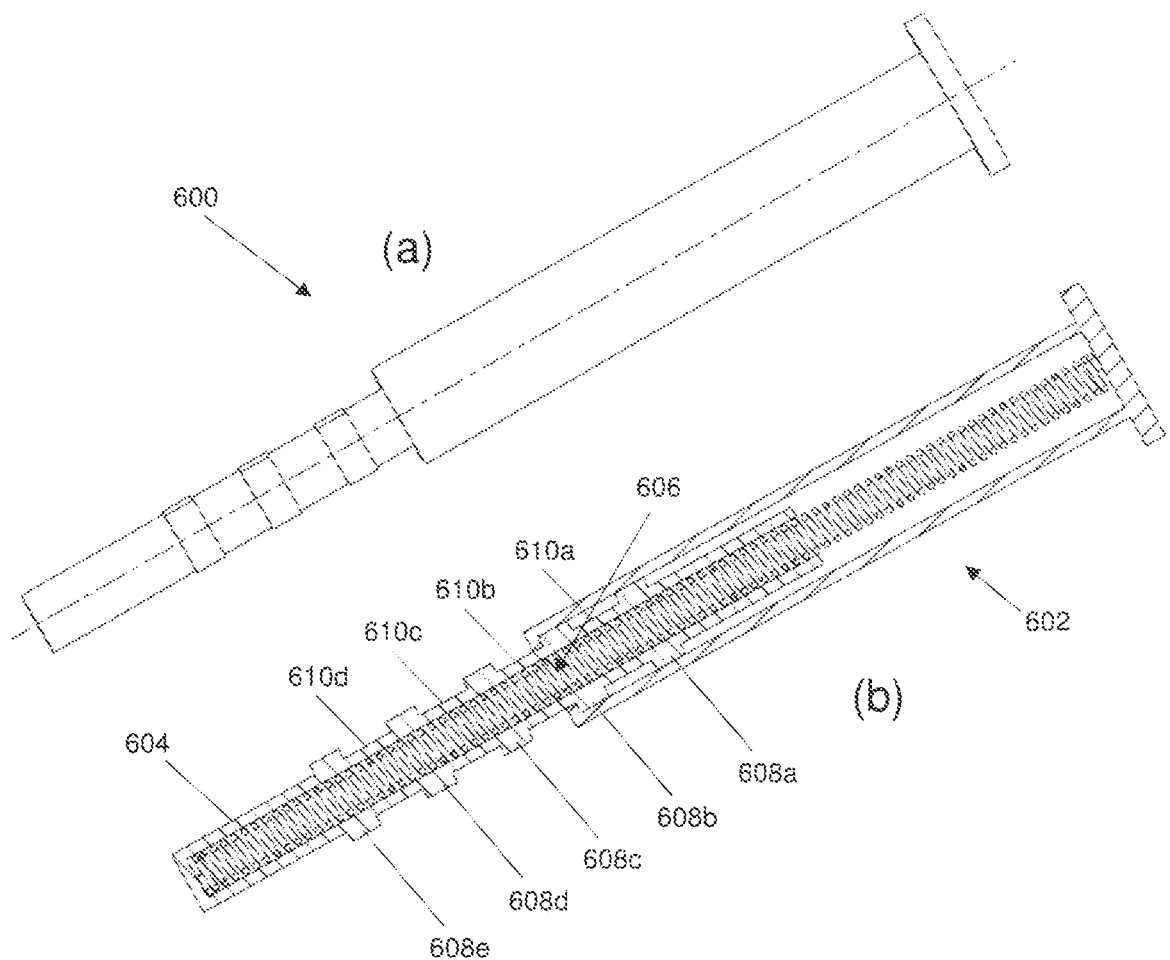
FIG. 6 shows an exemplary firing mechanism assembly.

FIG. 6 shows a schematic of a further arrangement of an assembly 600 for a firing mechanism. The assembly 600 comprises a rear cap 602 and a plunger 604. The rear cap 602 comprises a keyed aperture 606. At least one section of the plunger 604 has a cross section corresponding to and for passing through the keyed aperture 606. In the example shown in FIG. 6, five keyed sections 608a-608e of the plunger 604 have cross sections corresponding to the keyed aperture 606, but other numbers of such sections are possible. In the example shown in FIG. 6, the keyed aperture 606 has a length greater than a width thereof and may form a substantially rectangular or oblong shape. The width may substantially correspond to the width of the plunger 604 and the length may be greater than the width of the plunger 604. The plunger 604 also comprises lockout sections 610a-610d between the keyed sections 608a-608e configured to be rotatable within the keyed aperture 606. Rotation of the plunger 604 whilst one of the lockout sections 610a-610d is in the keyed aperture 606 allows the keying of the keyed aperture 606 to be out of alignment with the corresponding keying features 608a-608e of the plunger 604, which prevents further passage of the plunger 604 through the keyed aperture 606. In order to vary the connection between the plunger 604 and the rear cap 602, the plunger 604 may be rotated such that the keyed sections 608a-608e are aligned with the keyed aperture 606. The plunger 604 is passed through the keyed aperture 606 in either axial direction until the desired combined length of the assembly 600 is achieved. Then the plunger 604 is rotated whilst one of the lockout sections 610a-610d is within the keyed aperture 606 such that the keyed features 608a-608e and the keyed aperture are misaligned, thereby preventing further axial movement of the plunger rod 604 relative to the rear cap 602. FIG. 6a shows the assembly 600 with the plunger 604 rotated by 90 degrees relative to the plunger 604 in FIG. 6b.

FIGS. 7a and 7b show a further exemplary arrangement of an assembly 700 for a firing mechanism of an auto-injector. FIGS. 7a and 7b show partial sections through the assembly 700. In the exemplary arrangement, the rear cap 702 comprises a plurality of recesses 704a-704e. The plunger 706 comprises at least one elastic prong 708 having a radially inward facing projection 710. In exemplary arrangements the plunger 706 may comprise a plurality of elastic prongs 708.

The projection 710 is configured to be received within the recesses 704a-704e. The elastic prong 708 is biased radially inwards and has a resting state in which the projection 710 is received within a recess 704a, 704b. A force is required to displace the elastic prong 708 radially outwards to remove the projection 710 from a recess 704a, 704b. The projection 710 may have angled forward and/or rearward faces such that axial displacement of the plunger 706 with respect to the rear cap 702 provides the force required to remove the projection 710 from the recess 704a, 704b. That is, an axial force applied to the plunger 706 is translated to a radial force by interaction of the angled forward or rearward surface of the projection 710 with a sidewall of the recess 704a, 704b.

In the example of FIGS. 7a and 7b, the rear cap 702 is telescopically received within the plunger 706. This arrangement may apply to other exemplary assemblies described herein.

Figure 7:
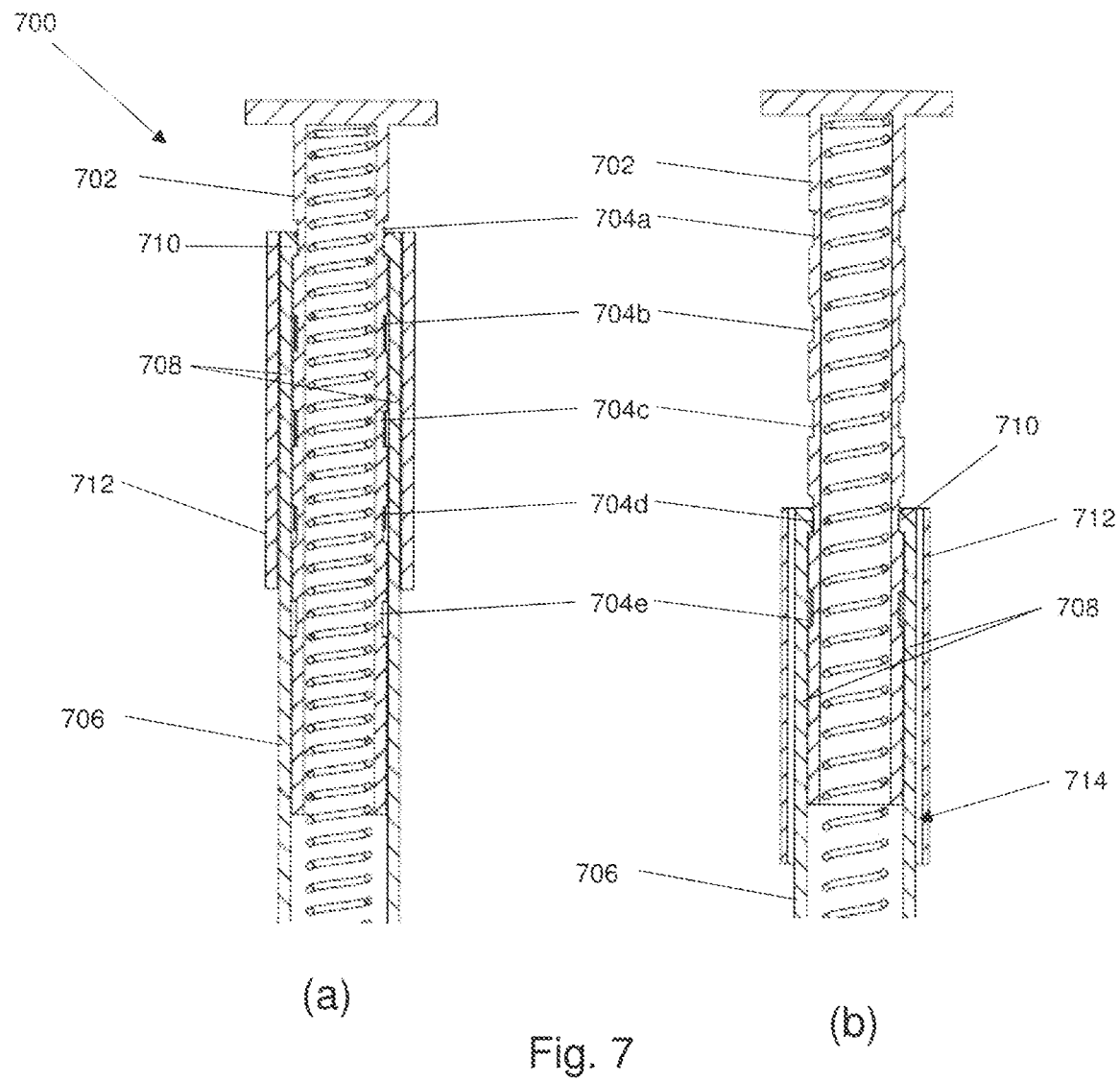
FIG. 7 panels (a) and (b) show an exemplary firing mechanism assembly.

The assembly 700 may further comprise a clutch 712 that is positioned around the plunger 706 and the rear cap 702. The clutch 712 has a varying internal diameter. In the example of FIG. 7, the clutch has at least two internal diameters, a first internal diameter at which an internal wall of the clutch prevents the elastic prong 708 from being displaced radially outwards (shown in FIG. 7a), and a second internal diameter that provides a space 714 between the elastic prong 708 and the internal wall of the clutch 712 (shown in FIG. 7b). The space is sufficient to allow radially outward displacement of the elastic prong 708 such that the projection 710 can be removed from the recess 704a-704e and placed into another.

It is noted that the difference in internal diameter of the clutch 712 that provides the space 714 need not extend around the entire internal circumference of the clutch 712. The second internal diameter may be obtained via a slot or other recess in the internal wall of the clutch 712.

During assembly, the cutch 712 is moved (in this case rotated) to provide the space 714 radially outwards from the elastic prong 708. The plunger 706 may then be axially displaced with respect to the rear cap 702 by first providing a force to displace the elastic prong 708 radially outwards and then axially moving the plunger 706 with respect to the rear cap 702. When the projection 710 is aligned with a recess 704a-704e that provides the desired combined length of the rear cap 702 and the plunger 706, the projection 710 will enter the recess 704a-704e under the bias of the elastic prong 708. The clutch is then moved such that the first internal diameter is presented to the elastic prong 708 restricting or preventing outward radial movement thereof.

In another arrangement, the clutch may have the first internal diameter at one axial position and the second internal diameter at a second axial position such that axial movement, as opposed to rotation, presents a different internal diameter to the elastic prong. Further, in arrangements where the plunger is received within the elongate member such as those shown in FIG. 5, the clutch may present the internal diameters to the elongate member and the elastic prong thereon.

Any of the assemblies for a firing mechanism of an auto-injector described above may be used in conjunction with the auto-injector 100 of FIGS. 1 and 2.

During assembly of the auto-injector, the assembly comprising the plunger and the rear cap is set using any of the methods and apparatus described herein. The plunger is connected to the elongate member of the rear cap. The connection is releasable in that upon activation of the auto-injector, the connection is released to allow relative axial movement of the plunger and the rear cap. Also, the connection may be made at any of a plurality of positions on the elongate member or the plunger. That is, one or both of the elongate member and the plunger may be configured to have a plurality of locations at which the connection may be made.

Accordingly, the combined axial length of the plunger and the rear cap is set to the desired length based on a fill volume (or bung position) of a syringe that the auto-injector is intended for use with. In so doing, the gap between the bung of the syringe, which sits at a position in the barrel that is dependent on the fill volume, is controlled. That is, if the combined axial length of the plunger and the rear cap is extended then the auto-injector may be used for syringes having a smaller fill volume, or otherwise having a bung that is initially positioned further forwards within the barrel, e.g. if the barrel is of a greater diameter but the fill volume remains the same. The start position of a forward end of the plunger is adjusted during assembly.

Once assembled, the user has no control over the combined length of the rear cap and the plunger.

Operation of the auto-injector 100 is described below using the reference numerals of the exemplary arrangement shown in FIGS. 1 and 2. As discussed above, other arrangements of the firing mechanism assembly may be used and the appropriate reference numerals may therefore be substituted into the following description.

In use, a user removes the cap 124 of the auto-injector 100, which in turn removes a rigid needle shield covering the needle. Removal of the cap exposes the lockout shroud 122, which protrudes from a forward end of the body 118.

The user places a forward end of the lockout shroud 122 against an injection site and pushes the auto-injector 100 downwards onto the injection site. This action pushes the lockout shroud 122 rearwards within the auto-injector 100. The lockout shroud interacts with the clutch 116 to rotate it. This may be done by forcing a surface (or pip) of the lockout shroud 122 against an angled surface on the clutch 116, which translates the rearward motion of the lockout shroud 122 into rotational motion of the clutch 116.

In some arrangements, an insertion spring may be activated by the action of pushing the auto-injector 100 onto the injection site and the insertion spring may drive the syringe forwards within the device to insert the needle into the injection site. In other arrangements, the force applied by the drive spring 112 acting against the bung may be used to insert the needle. In yet further arrangements, the syringe may be fixed in relation to the injection device 100 and the force applied by the user when pushing the auto-injector 100 onto the injection site may insert the needle into the injection site.

As the clutch 116 is rotationally coupled to the plunger 106, rotation of the clutch 116 causes rotation of the plunger 106. In some arrangements, the clutch 116 may have an internal track located on an internal wall thereof and that receives a lug of the plunger 106. The lug may be the same as the lug 306 described with reference to FIGS. 3a and 3b. Rotation of the plunger 106 with respect to the rear cap 104 releases the connection between the rear cap 104 and the plunger 106, allowing the plunger 106 to be driven forwards under force of the drive spring 112. In the examples of FIGS. 1-4, this is provided by rotating the lug 306 of the plunger rod 106 out of whichever recess 308a, 308b, 408a-408c the lug 306 was positioned in and into the axial channel 310. The lug 306 is thereby allowed to travel forwards within the channel 310.

The drive spring 112 then acts against the plunger 106 and the rear cap 104. Because the rear cap 104 is fixed within the auto-injector 100, the force delivered by the drive spring 112 acts to drive the plunger 106 into the barrel of the syringe. Because the gap between the forward end of the plunger 106 and the bung 202 has been controlled during assembly, the plunger 106 does not accelerate above a safe velocity that would risk damage to the syringe 200 or harm or discomfort to the subject of the injection.

After delivery of the contents of the syringe 200, the lockout shroud is deployed under force of the lockout spring 120 in any of a number of ways that will be apparent to the skilled person.

FIGS. 3-5 and 7 show arrangements in which a direct releasable connection is made between the plunger and the elongate member. This arrangement is less complex but results in an activation point (in some cases above, the lug 308) being in different axial positions. Therefore, the activation mechanism needs to adapt to suit. FIGS. 6 and 8-10 show arrangements in which the releasable connection is made indirectly to the elongate member via a plunger carrier. The plunger carrier is typically fixed in relation to the elongate member until activation of the injection device. The connection of the plunger to the plunger rod carrier may be made at a plurality of locations positions for controlling the axial length of the assembly.

Figure 8A:
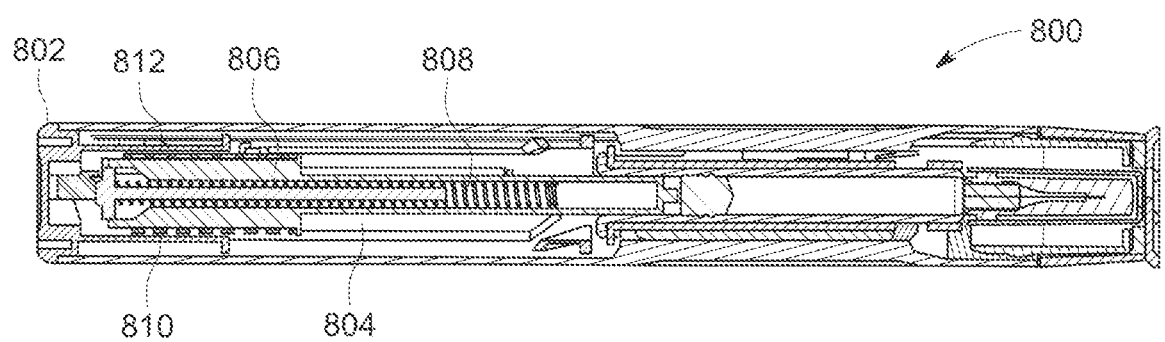
FIGS. 8a-8b show sections through an exemplary auto-injector.
Figure 8B:
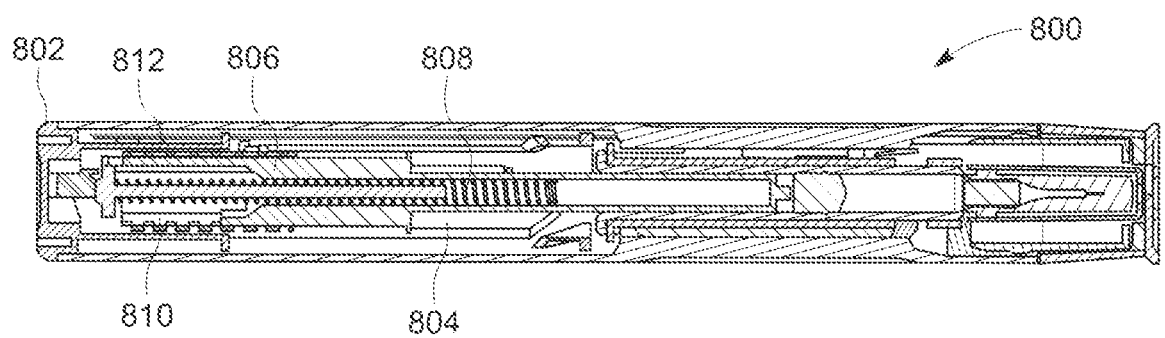

FIGS. 8a and 8b show an exemplary injection device 800. The injection device 800 comprises an assembly for use as a firing mechanism. The assembly comprises a rear cap 802 comprising an elongate member 804, a plunger 806, a plunger driver 808 and a plunger carrier 810.

The plunger carrier 810 is releasably connected to the elongate member 804, wherein the connection is released on activation of the injection device 800. The releasable connection may be achieved in any way described herein, or by any other means that will be known to a skilled person.

The plunger 806 is connected to the plunger carrier 810 at one of a plurality of positions to control the overall axial length of the assembly. This connection is made during construction of the assembly and/or the injection device 800. In the exemplary arrangement of FIGS. 8a and 8b, the plunger carrier 810 comprises a plurality of recesses 812 into which a lug (not visible in FIGS. 8a and 8b) on the plunger 806 may be located, each recess having a different axial position. FIG. 8a shows the connection between the plunger 806 and the plunger carrier 810 made at a first position, and FIG. 8b shows the connection between the plunger 806 and the plunger carrier 810 made at a second position axially further forwards than the first position. As can be seen, the forward end of the plunger is also further forward in FIG. 8b.

Figure 9A:
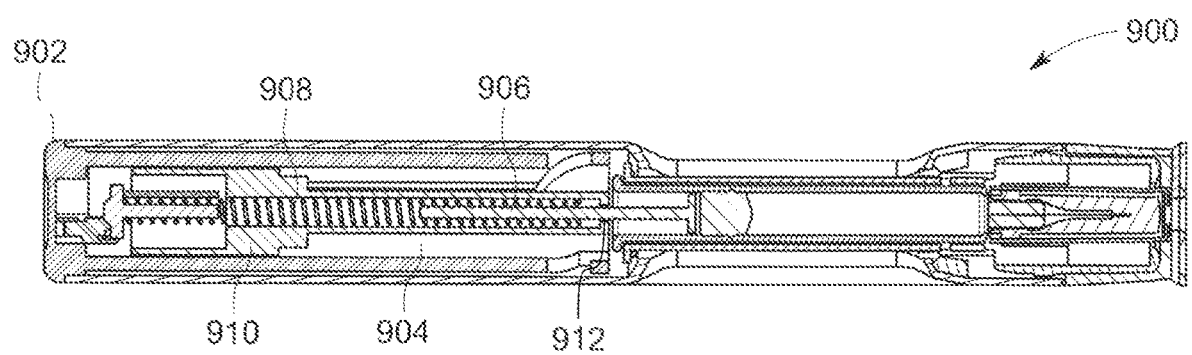
FIGS. 9a-9b show sections through an exemplary auto-injector.
Figure 9B:
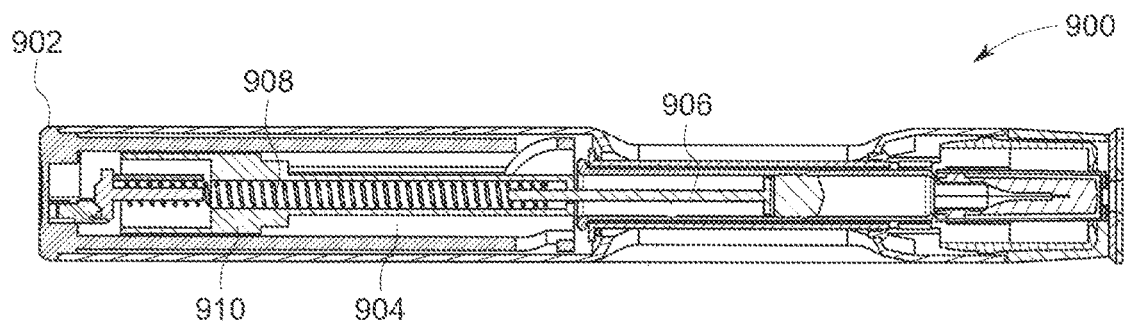

FIGS. 9a and 9b show a further exemplary injection device 900. The injection device 900 comprises an assembly for use as a firing mechanism. The assembly comprises a rear cap 902 comprising an elongate member 904, a plunger 906, a plunger driver 908 and a plunger carrier 910. As with the injection device 800 in FIGS. 8a and 8b, the plunger carrier 910 is releasably connected to the elongate member 904, wherein the connection is released on activation of the injection device 900.

The plunger 906 comprises a thread at least partially along its length. The plunger carrier 910 comprises a thread engagement feature that engages the thread of the plunger 906. The thread engagement feature can be a further thread corresponding to the thread on the plunger 906, but need not be a full thread and may comprise one or more projections arranged to engage the thread. In the example shown in FIGS. 9a and 9b, the plunger carrier 910 comprises a threaded aperture 912 in a forward end. Rotation of the plunger 906 relative to the plunger carrier 910 controls the extension of the plunger 906 from the threaded aperture 912. This controls the axial length of the assembly and the start point of the forward end of the plunger 906. It is noted that for the purposes of describing the invention, the phrase "connected to the elongate member at one of a plurality of positions for controlling the axial length of the assembly"

encompasses a continuous connection arrangements, such as the continuous nature of the controllability of the connection of the plunger 906 to the plunger carrier 910 (i.e. the threaded arrangement).

Figure 10A:
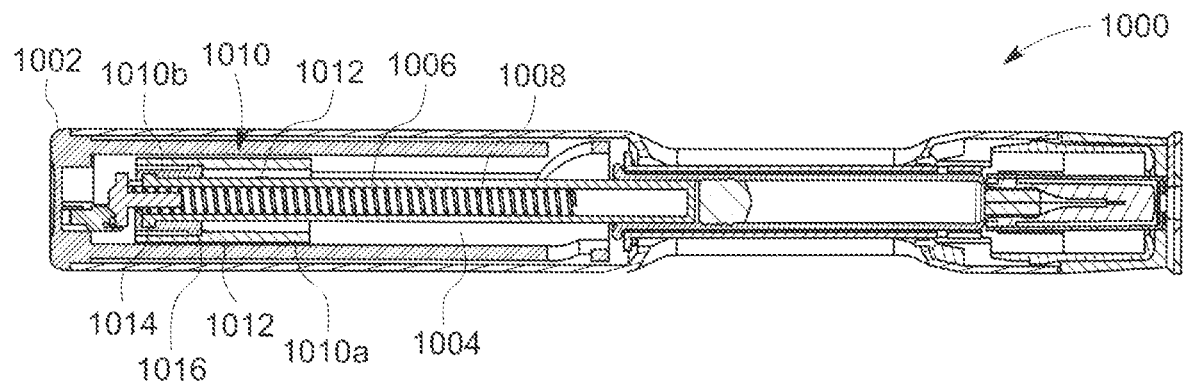
FIGS. 10a-10c show sections through an exemplary auto-injector.
Figure 10B:
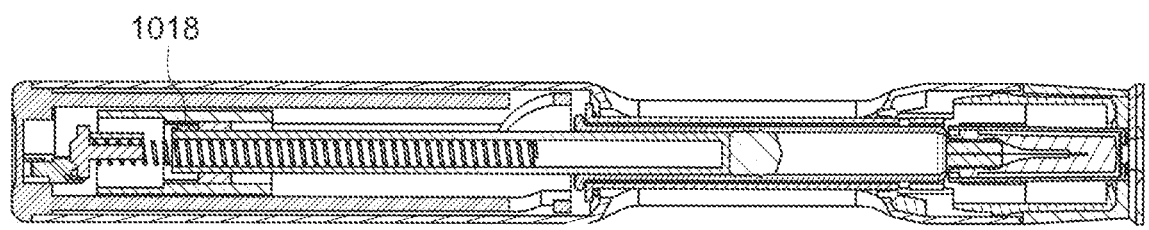
Figure 10C:
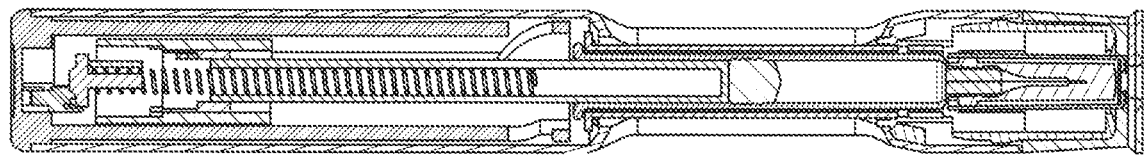

FIGS. 10*a-c* show a further exemplary injection device 1000. The injection device 1000 comprises an assembly for use as a firing mechanism. The assembly comprises a rear cap 1002 comprising an elongate member 1004, a plunger 1006, a plunger driver 1008 and a plunger carrier 1010. As with the injection devices 800 and 900, the plunger carrier 1010 is releasably connected to the elongate member 1004, wherein the connection is released on activation of the injection device 1000. In addition the plunger carrier 1010 comprises two parts 1010*a* and 1010*b*, as explained below.

A first part 1010*a* of the plunger carrier 1010 comprises a plurality of abutment surfaces 1012 at different axial positions on the plunger carrier 1010 and that, in the example shown are in a stepped arrangement, although they may be at the forward end of discrete channels.

In one arrangement not shown in FIG. 10, the plunger 1006 may include a corresponding abutment surface 1014 that is configured to abut the abutment surfaces of the first part 1010*a* of the plunger carrier 1010. In such arrangements, the second part 1010*b* of the plunger carrier 1010 may not be required. The plunger 1006 may be rotated to a correct alignment with the plunger carrier 1010 and then the abutment surfaces engaged. By selecting the rotational alignment, the extension of the plunger 1006 and therefore the axial length of the assembly is controlled.

In the arrangement shown in FIGS. 10*a-c*, the plunger carrier 1010 also comprises a second part 1010*b*. The second part 1010*b* comprises a first abutment surface 1016 for abutment with the abutment surfaces of the first part 1010*a* of the plunger carrier 1010. The second part 1010*b* may be rotationally aligned with the first part 1010*a* of the plunger carrier 1010 such that the first abutment surface of the second part 1010*b* meets the correct abutment surface of the first part 1010*a*. The second part 1010*b* also comprises a plurality of second abutment surfaces 1018 that are arranged to abut the abutment surface 1014 of the plunger 1006. Accordingly, the plunger 1006 may be rotationally aligned with the second part 1010*b* such that the abutment surface 1014 of the plunger 1006 is aligned with the correct second abutment surface 1018 of the second part 1010*b*.

During construction of the assembly, the second part 1010*b* is inserted into the first part 1010*a*, with the correct rotational alignment. Then the plunger 1006 is inserted into the second part 1010*b*, again with the correct rotational alignment. When the injection device 1000 is activated, the first part 1010*a*, second part 1010*b* and the plunger 1006 move forwards together.

The use of a plurality of abutment surfaces on the first part 1010*a* and the second part 1010*b* allow for greater control over the axial length of the assembly and therefore of the starting point of the forward end of the plunger 1006. FIGS. 10*a-c* show different configurations in which the abutment surface 1014 of the plunger 1006 abuts different ones of the second abutment surfaces 1018 of the second part 1010*b*, and the first abutment surface 1016 of the second part 1010*b* abuts different abutment surfaces 1012 of the first part 1010*a*.

The injection devices 800, 900, 1000 of FIGS. 8-10 operate in a similar fashion to that of the injection device 100, operation of which is described above. The principal difference is that the connection between the plunger carrier and the elongate member is released on activation of the device and the plunger carrier and plunger are driven forwards together by the plunger driver.

The skilled person will be able to envisage other assemblies, auto-injectors and features thereof without departing from the scope of the appended claims. In particular, it is noted that one or more features included in one or more drawings may be integrated into auto-injectors shown in other drawings, as will be appreciated by the skilled person.

The invention claimed is:

1. An assembly for a firing mechanism for use in an injection device and comprising:
   a rear cap having an elongate member extending axially forwards when installed within the injection device;
   a plunger carrier releasably connected to the elongate member and fixed in position relative to the elongate member before release from the elongate member;
   a plunger releasably connected to the elongate member via the plunger carrier and, upon release of the connection between the plunger carrier and the elongate member, axially displaceable in a forward direction; and
   a plunger driver to drive the plunger axially forwards upon release of the connection between the plunger carrier and the elongate member, the plunger driver positioned between the rear cap and the plunger and received within the plunger such that a first end of the plunger driver abuts a forward end of the plunger,
   wherein the plunger and the rear cap define an axial length of the assembly, which in turn determines a start position of a forward end of the plunger before release of the connection to the elongate member,
   wherein one or both of the plunger and the plunger carrier comprises a plurality of connection features for connection between the plunger and the plunger carrier during construction of the assembly, the plurality of connection features defining a plurality of different positions at which the plunger is releasably connectable to the plunger carrier, each of the plurality of different positions defining a different start position of the forward end of the plunger,
   and wherein, during construction of the assembly, the plunger is releasably connectable to the plunger carrier at one of the plurality of positions defined by the plurality of connection features for controlling the axial length of the assembly and for defining the start position of the forward end of the plunger.

2. The assembly according to claim 1, wherein the plurality of connection features comprises a plurality of recesses or apertures on the plunger carrier, and wherein the plunger comprises a lug configured to be received in one of the plurality of recesses or apertures.

3. The assembly according to claim 1, wherein the plunger is connectable to the plunger carrier by a thread on one of the plunger and the plunger carrier and a thread engagement feature on the other of the plunger and the plunger carrier.

4. The assembly according to claim 1, wherein the plunger carrier comprises a plurality of abutment surfaces at a plurality of axial positions on the plunger carrier, and wherein the plunger comprises a corresponding abutment surface configured to abut one of the plurality of abutment surfaces of the plunger carrier.

5. The assembly according to claim 4, wherein the plunger is rotatable to align the corresponding abutment surface of the plunger with one of the plurality of abutment surfaces on the plunger carrier and facilitate engagement therebetween.

6. The assembly according to claim 4, wherein the plurality of abutment surfaces of the plunger carrier are in a stepped arrangement.

7. The assembly according to claim 1, wherein the plunger carrier comprises a first part comprising a plurality of abutment surfaces at a plurality of axial positions on the first part, and a second part comprising a first abutment surface for abutment with one of the plurality of abutment surfaces of the first part.

8. The assembly according to claim 7, wherein the second part is rotatable to align the first abutment surface with one of the plurality of abutment surfaces of the first part.

9. The assembly according to claim 7, wherein the second part further comprises a plurality of second abutment surfaces, and wherein the plunger comprises a corresponding abutment surface configured to abut one of the plurality of second abutment surfaces.

10. The assembly according to claim 9, wherein the plunger is rotatable to align the corresponding abutment surface with the one of the plurality of second abutment surfaces.

11. The assembly according to claim 9, wherein the second part is received within the first part, and wherein the plunger is received within the second part.

12. The assembly according to claim 1, wherein the plunger driver is further configured to drive the plunger carrier axially forwards upon release of the connection between the plunger carrier and the elongate member.

13. The assembly according to claim 1, wherein the plunger is telescopically received within the elongate member.

14. The assembly according to claim 1, wherein a second end of the plunger driver is fixed with respect to the rear cap.

15. An injection device comprising the assembly according to claim 1.

16. A method of constructing an assembly for a firing mechanism for an injection device, the method comprising:
  releasably connecting, indirectly, a plunger to an elongate member of a rear cap via a plunger carrier, the plunger carrier releasably connected to the elongate member and fixed in position relative to the elongate member before release from the elongate member, the plunger being axially displaceable in a forward direction by a plunger driver upon release of the connection between the plunger carrier and the elongate member,
  wherein the plunger driver is positioned between the rear cap and the plunger and received within the plunger such that a first end of the plunger driver abuts a forward end of the plunger,
  wherein the plunger and the rear cap define an axial length of the assembly, which in turn determines a start position of a forward end of the plunger before release of the connection to the elongate member,
  wherein the indirect releasable connection of the plunger to the elongate member is made using some of a plurality of connection features on one or both of the plunger and the plunger carrier, the plurality of connection features defining a plurality of different positions at which the plunger is releasably connectable to the plunger carrier and each of the different positions defining a different start position of the forward end of the plunger, and
  wherein the releasable connection is made at any of the plurality of positions defined by the connection features to control the axial length of the assembly and to select the different start positions of the forward end of the plunger.

* * * * *